(12) United States Patent
Artale et al.

(10) Patent No.: US 8,215,182 B2
(45) Date of Patent: Jul. 10, 2012

(54) APPARATUS AND METHOD FOR MEASURING PRESSURE BETWEEN JAW MEMBERS

(75) Inventors: Ryan C. Artale, Boulder, CO (US); J. Bruce Dunne, Longmont, CO (US); Blake Randolph, Columbia, MO (US); Brandon Risk, Boulder, CO (US); Colin P. Carr, Boulder, CO (US); Leif Cook, Louisville, CO (US); David M. Garrison, Longmont, CO (US); Jeffrey D. Ipsen, Broomfield, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 172 days.

(21) Appl. No.: 12/597,213

(22) PCT Filed: Apr. 25, 2008

(86) PCT No.: PCT/US2008/061498
§ 371 (c)(1),
(2), (4) Date: Jul. 19, 2010

(87) PCT Pub. No.: WO2008/134471
PCT Pub. Date: Nov. 6, 2008

(65) Prior Publication Data
US 2011/0036183 A1    Feb. 17, 2011

Related U.S. Application Data

(60) Provisional application No. 60/914,254, filed on Apr. 26, 2007.

(51) Int. Cl.
*G01N 3/02* (2006.01)

(52) U.S. Cl. ............................................. 73/860
(58) Field of Classification Search ............ 73/856–860
See application file for complete search history.

(56) References Cited

U.S. PATENT DOCUMENTS

| 702,472 A | 6/1902 | Pignolet |
| 4,022,453 A * | 5/1977 | Durgan ........................... 269/71 |

(Continued)

FOREIGN PATENT DOCUMENTS

DE    2415263    10/1975

(Continued)

OTHER PUBLICATIONS

U.S. Appl. No. 09/387,883, filed Sep. 1, 1999.

(Continued)

*Primary Examiner* — Max Noori (57) ABSTRACT

Testing system for measuring closure pressure between jaw members of electrosurgical forceps. The testing system includes a testing platform, a pair of selectively adjustable instrument supports, a testing stand. The platform has an elongated bed that supports an instrument rest, which supports the electrosurgical forceps. The pair of instrument supports are associated with the elongated bed and secure the forceps atop the elongated bed. The testing stand is disposed at a distal end of the elongated bed and supports a piece of testing material. The testing stand includes a layer of visco-elastic material and a pressure sensitive film. The layer of visco-elastic material forms a pocket. The pressure sensitive film is disposed within the pocket of the visco-elastic layer. The pressure sensitive film is adapted to electromechanically communicate with a diagnostic system to measure the closure pressure between jaw members when they are in a clamped configuration.

23 Claims, 4 Drawing Sheets

U.S. PATENT DOCUMENTS

| | | | |
|---|---|---|---|
| D249,549 S | 9/1978 | Pike | |
| 4,236,470 A | 12/1980 | Stenson | |
| 4,270,390 A * | 6/1981 | Kimball et al. | 73/663 |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,217,457 A | 6/1993 | Delahuerga et al. | |
| D343,453 S | 1/1994 | Noda | |
| D348,930 S | 7/1994 | Olson | |
| D349,341 S | 8/1994 | Lichtman et al. | |
| 5,367,250 A | 11/1994 | Whisenand | |
| D354,564 S | 1/1995 | Medema | |
| 5,409,763 A | 4/1995 | Serizawa et al. | |
| D358,887 S | 5/1995 | Feinberg | |
| 5,562,720 A | 10/1996 | Stern et al. | |
| 5,638,003 A | 6/1997 | Hall | |
| D384,413 S | 9/1997 | Zlock et al. | |
| D402,028 S | 12/1998 | Grimm et al. | |
| 5,954,460 A * | 9/1999 | Degen et al. | 408/112 |
| D416,089 S | 11/1999 | Barton et al. | |
| D424,694 S | 5/2000 | Tetzlaff et al. | |
| D425,201 S | 5/2000 | Tetzlaff et al. | |
| D449,886 S | 10/2001 | Tetzlaff et al. | |
| D454,951 S | 3/2002 | Bon | |
| D457,958 S | 5/2002 | Dycus et al. | |
| D457,959 S | 5/2002 | Tetzlaff et al. | |
| D465,281 S | 11/2002 | Lang | |
| D466,209 S | 11/2002 | Bon | |
| 6,582,451 B1 * | 6/2003 | Marucci et al. | 606/207 |
| 6,679,882 B1 | 1/2004 | Kornerup | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| 7,169,145 B2 | 1/2007 | Isaacson et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,982,477 B2 * | 7/2011 | Ghadaksaz | 324/750.09 |
| 8,034,049 B2 * | 10/2011 | Odom et al. | 606/34 |
| 2003/0229344 A1 | 12/2003 | Dycus et al. | |
| 2006/0064086 A1 | 3/2006 | Odom | |
| 2006/0229666 A1 | 10/2006 | Suzuki et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 02617 | 12/2005 |
| DE | 20 2007 00931 | 10/2007 |
| DE | 19738457 | 1/2009 |
| EP | 1159926 | 12/2001 |
| EP | 1767163 | 3/2007 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | O9010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 96/13218 | 5/1996 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 09/597,328, filed Jun. 9, 2000.
U.S. Appl. No. 12/336,970, filed Dec. 17, 2008.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/556,025, filed Sep. 9, 2009.
U.S. Appl. No. 12/553,509, filed Sep. 3, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.

U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/833,270, filed Jul. 9, 2010.
U.S. Appl. No. 12/843,384, filed Jul. 26, 2010.
U.S. Appl. No. 12/845,203, filed Jul. 28, 2010.
U.S. Appl. No. 12/846,602, filed Jul. 29, 2010.
U.S. Appl. No. 12/853,896, filed Aug. 10, 2010.
U.S. Appl. No. 12/859,896, filed Aug. 20, 2010.
U.S. Appl. No. 12/859,985, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,662, filed Sep. 7, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/879,505, filed Sep. 10, 2010.
U.S. Appl. No. 12/882,304, filed Sep. 15, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Crouch, J.R. , et al. "A Velocity-Dependent Model for Needle Insertion in Soft Tissue", MICCAI 2005, LNCS 3750, pp. 624-632, 2005.
Tinkcler L.F., "Combined Diathermy and Suction Forceps" , Feb. 6, 1967 (Feb. 6, 1965), British Medical Journal Feb. 6, 1976, Vol. 1, nr. 5431 p. 361, Issn: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands 17-21 Aug. 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan., 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'L Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'L Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'L Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended-EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/USO4/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

APPARATUS AND METHOD FOR MEASURING PRESSURE BETWEEN JAW MEMBERS

CROSS-REFERENCE TO A RELATED APPLICATION

The present application claims the benefit of and priority to U.S. Provisional Application Ser. No. 60/914,254, filed on Apr. 26, 2007, the entire content of which is hereby incorporated by reference.

BACKGROUND

1. Technical Field

The present disclosure relates to an electrosurgical forceps and more particularly, the present disclosure relates to an apparatus and method for measuring the pressure between two jaw members when clamped on tissue or a tissue-like substance.

The present disclosure also relates to an apparatus and method for simulating pressure on tissue and tissue response.

2. Description of Related Art

Open and endoscopic electrosurgical forceps utilize both mechanical clamping action and electrical energy to effect hemostasis by heating the tissue and blood vessels to coagulate, cauterize and/or seal tissue. Open electrosurgical forceps, as the name infers, are typically utilized during open surgical procedure where a surgeon has open access to the surgical cavity. Endoscopic instruments, on the other hand, are typically inserted into the patient through a cannula, or port, which has been made with a trocar and the surgeon remotely actuates the instrument to treat tissue.

Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

In order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

Accurate application of closure forces between electrically conductive surfaces, i.e., jaw members, is important to limit undesirable electrical abnormalities or tissue damage, e.g., it may cause the opposing electrodes to come into close contact with one another which may result in a short circuit and a small closure force may cause premature movement of the tissue during compression and prior to activation. As a result thereof, providing an instrument which consistently provides the appropriate closure force between opposing electrode within a preferred pressure range will enhance the chances of a successful seal.

It has been found that the pressure range for assuring a consistent and effective seal is between about 3 kg/cm$^2$ to about 16 kg/cm$^2$ and, desirably, within a working range of 7 kg/cm$^2$ to 13 kg/cm$^2$. Manufacturing an instrument which is capable of providing a closure pressure within this working range has been shown to be effective for sealing arteries, tissues and other vascular bundles.

SUMMARY

The present disclosure relates to a testing system for measuring a closure pressure between opposing jaw members of an electrosurgical forceps. The testing system includes a testing platform, a pair of selectively adjustable instrument supports, and a testing stand. The testing platform has an elongated bed that supports an instrument rest, which in turn, supports the electrosurgical forceps. The pair of selectively adjustable instrument supports are operatively associated with the elongated bed and are positioned to secure the forceps atop the elongated bed. The testing stand is disposed at a distal end of the elongated bed and configured to support a piece of testing material. The testing stand includes a layer of visco-elastic material and a pressure sensitive film. The layer of visco-elastic material is configured to form a pocket therebetween. The pressure sensitive film is disposed within the pocket of the visco-elastic layer. The pressure sensitive film is adapted to electro-mechanically communicate with a diagnostic system to measure the closure pressure between jaw members when the jaw members are disposed in a clamped configuration.

Additionally, the instrument supports each define a notch configured to support a shaft of the electrosurgical forceps therewithin. The testing stand includes a testing clamp configured to secure the testing material to the testing stand. The testing clamp is hingedly connected to the testing stand by at least one hinge. The testing clamp is selectively moveable between an open position and a closed position, wherein when the testing clamp is in the open position the testing material is insertable therein, and when the testing clamp is in the closed position the testing material is secured therein.

The testing clamp is biased to the closed position by a biasing member. The testing clamp is in a U-shaped configuration to define an area such that when the testing material is secured to the testing clamp, a portion of the testing material is exposed in the area of the testing clamp. The visco-elastic material includes two opposing material layers. The pressure sensitive film is disposed between the two opposing material layers in operative communication with an electrical lead. The electrical lead may be connected to a meter, a pressure gauge, a computer diagnostic system or a display apparatus.

In another embodiment, a testing system for measuring a closure pressure between opposing jaw members of an electrosurgical forceps includes a testing platform, a pair of selectively adjustable instrument supports and a testing stand. The testing platform includes an elongated bed, which in turn, is configured to support the electrosurgical forceps. The pair of selectively adjustable instrument supports are operatively associated with the elongated bed and positioned to secure the forceps relative to the platform. The testing stand is disposed at a distal end of the elongated bed and configured to support a testing material thereon. The testing material includes a visco-elastic material that supports a pressure sensitive film. The pressure sensitive film is adapted to electromechanically communicate with a diagnostic system to measure the closure pressure between the jaw members when the jaw members are clamped on the testing material.

In addition, the testing stand includes a testing clamp in order to secure the testing material to the testing stand. The testing clamp is hingedly connected to the testing stand by a hinge is selectively moveable between an open position and a closed position. When the testing clamp is in the open position the testing material is insertable therein, and when the testing clamp is in the closed position the testing material is secured therein. Further, the testing clamp is biased to the closed position by a biasing member. The testing clamp may have a U-shaped configuration to define an area such that when the testing material is secured to the testing clamp, a portion of the testing material is exposed in the area of the testing clamp.

The present disclosure also relates to a method for testing a closure pressure of an electrosurgical forceps. The method includes the steps of: providing a forceps having an end effector assembly including two opposing jaw members; providing a testing fixture configured to support the forceps; providing a testing material which includes two layers of visco-elastic material having a pressure sensitive film disposed between the layers; securing testing material to the testing stand; opening the jaw members of the end effector assembly to receive the testing material; closing and clamping the jaw members onto the testing material; and analyzing a pressure distribution between the opposing jaw members.

The method for testing a closure pressure of an electrosurgical forceps also includes the steps of verifying that the pressure between the jaw members is between about 3 kg/cm$^2$ to about 16 kg/cm$^2$, or, more particularly, between about 7 kg/cm$^2$ to about 13 kg/cm$^2$; connecting the pressure sensitive film to a visual display; supporting a shaft of the forceps in or on at least one support of the test fixture; providing a test fixture having a pair of supports configured to support the shaft of the forceps; and adjusting a location of the supports along a length of the shaft.

BRIEF DESCRIPTION OF THE DRAWINGS

Various embodiments of the subject instrument are described herein with reference to the drawings wherein.

DETAILED DESCRIPTION

The present disclosure relates to a testing system 400 which provides accurate, repeatable and real time pressure analysis to enable instrument manufacturers and/or quality control experts to make reliable design decisions during the course of product development and assembly line manufacturing.

Figure 1:
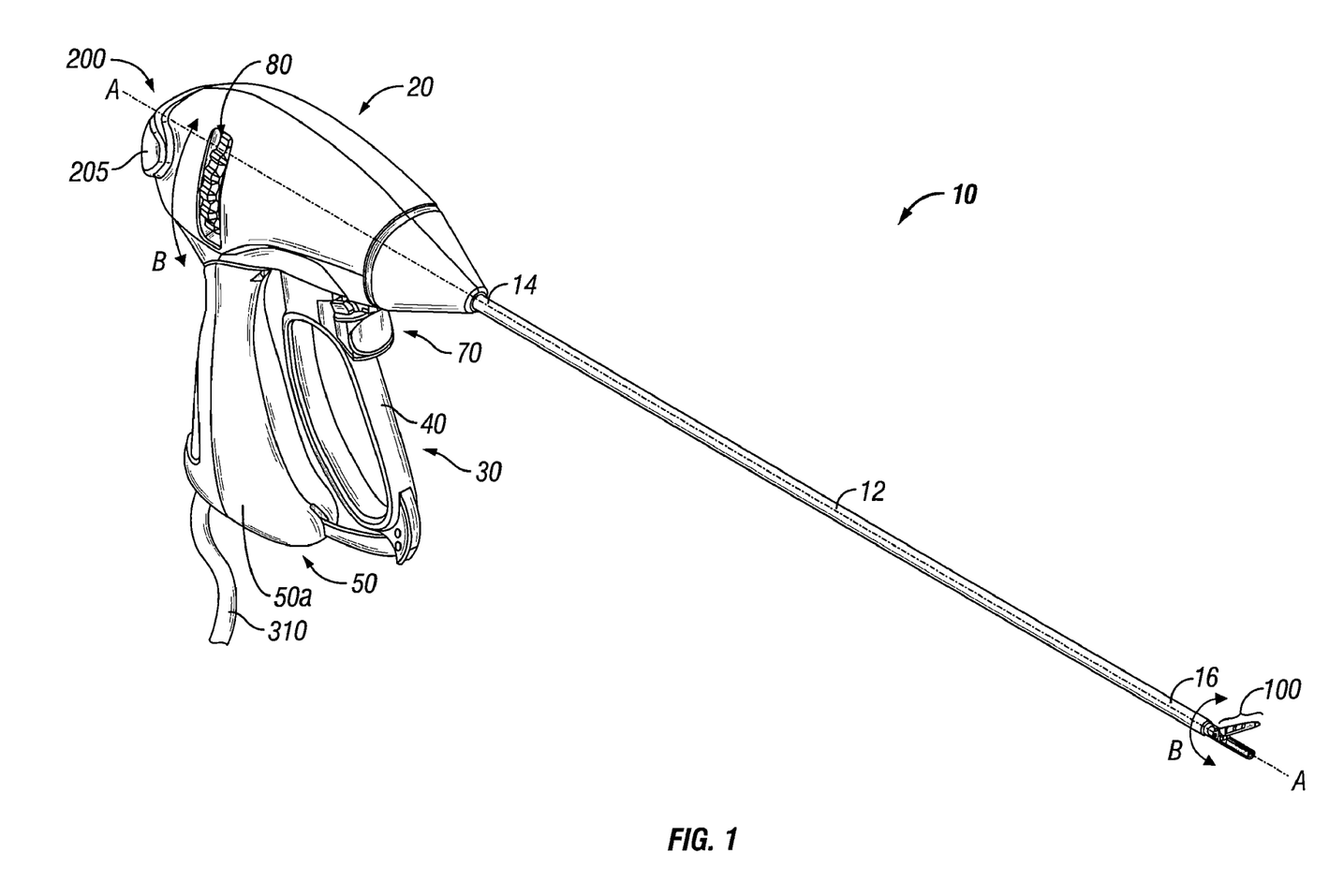
FIG. 1 is a perspective view of an endoscopic bipolar forceps showing a housing, a shaft and an end effector assembly for use with a testing system according to the present disclosure.

Turning initially to FIG. 1, an endoscopic bipolar forceps 10 for use within the below-described testing fixture is shown and generally includes a housing 20, a handle assembly 30, a rotating assembly 80, a trigger assembly 70 and an end effector assembly 100, which mutually cooperate to grasp, seal and divide tubular vessels and vascular tissue. Although the majority of the figure drawings depict an endoscopic bipolar forceps 10 for use in connection with endoscopic surgical procedures, the present disclosure, in particular, the testing material may be used to test the closure pressure for forceps used with more traditional open surgical procedures. For the purposes herein, the testing system 400 is described for use with an endoscopic forceps 10 is described in terms of the instrument as shown, however, it is contemplated that an open version of the forceps may also include the same or similar operating components and features as described below.

Forceps 10 includes a shaft 12 which has a distal end 16 dimensioned to mechanically engage the end effector assembly 100 and a proximal end 14, which mechanically engages the housing 20. Details of how the distal end 16 of the shaft 12 connects to the end effector assembly 100 and how the proximal end 14 connects to the housing 20 are described in more detail with respect to commonly-owned U.S. Pat. Nos. 7,156,846 and 7,150,749; and U.S. Publication No. 2006-0129146, the entire contents of all of which are incorporated by reference herein. In the drawings and in the descriptions which follow, the term "proximal," as is traditional, will refer to the end of the forceps 10 which is closer to the user, while the term "distal" will refer to the end which is farther from the user.

As best seen in FIG. 1, forceps 10 also includes an electrosurgical cable 310 which connects the forceps 10 to a source of electrosurgical energy, e.g., a generator (not shown). It is contemplated that generators such as those sold by Valleylab—a division of Tyco Healthcare LP, located in Boulder, Colo. are used as a source of electrosurgical energy, e.g., FORCE EZ™ Electrosurgical Generator, FORCE FX™ Electrosurgical Generator, FORCE 1C™, FORCE 2™ Generator, SurgiStat™ II, and Force Triad™.

Cable 310 is internally divided into cable leads (not shown) which each transmit electrosurgical energy through their respective feed paths through the forceps 10 to the end effector assembly 100 as explained in more detail with respect to the above-identified incorporated applications. Leads extend from cable 310 and connect to a hand switch or toggle switch 200.

Switch 200 includes an ergonomically dimensioned toggle plate 205 having a pair of wings which may conform to the outer shape of housing 20 (once assembled). Switch 200 permits the user to selectively activate the forceps 10 in a variety of different orientations, i.e., multi-oriented activation, which simplifies activation. When the toggle plate 205 is depressed, electrosurgical energy is transferred through leads a series of leads (not shown) to jaw members 110 and 120, respectively.

Handle assembly 30 includes a fixed handle 50 and a movable handle 40. Fixed handle 50 is integrally associated with housing 20 and handle 40 is movable relative to fixed handle 50. Rotating assembly 80 is integrally associated with the housing 20 and is rotatable along arrow "B" approximately 180 degrees in either direction about a longitudinal axis "A-A" (See FIG. 4). Details of the rotating assembly 80 are described in more detail with respect to the above-identified incorporated applications.

End effector assembly 100 includes opposing jaw members 110 and 120 which cooperate to effectively grasp tissue for sealing purposes. The end effector assembly 100 is designed as a unilateral assembly, i.e., jaw member 120 is fixed relative to the shaft 12 and jaw member 110 pivots about a pivot pin 103 to grasp tissue. A bilateral assembly is also contemplated. Movable handle 40 of handle assembly 30 is ultimately connected to a drive assembly (not shown) which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

A knife channel (not shown) runs through the center of the jaw members 110 and 120, respectively, such that a blade (not shown) can cut the tissue grasped between the jaw members 110 and 120 when the jaw members 110 and 120 are in a closed position. Trigger assembly 70 mounts atop movable handle 40 and cooperates to selectively translate the blade through a tissue.

The handle 40 in combination with the internal drive assembly (not shown) assures consistent, uniform and accurate closure pressure about the tissue within the desired working pressure range of about 3 kg/cm$^2$ to about 16 kg/cm$^2$ and, preferably, about 7 kg/cm$^2$ to about 13 kg/cm$^2$. By controlling the intensity, frequency and duration of the electrosurgical energy applied to the tissue, the user can either cauterize, coagulate/desiccate, seal and/or simply reduce or slow bleeding.

As mentioned above, two mechanical factors play an important role in determining the resulting thickness of the sealed tissue and effectiveness of the seal, i.e., the pressure applied between opposing jaw members 110 and 120 and the gap distance between the opposing sealing surfaces of the jaw members 110 and 120 during the sealing process. However, thickness of the resulting tissue seal cannot be adequately controlled by force alone. In other words, too much force and the two jaw members 110 and 120 would touch and possibly short resulting in little energy traveling through the tissue thus resulting in a bad tissue seal 450. Too little force and the seal would be too thick.

Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness which is an indication of a good seal.

With respect to controlling the gap distance a stop member (not shown) extends a predetermined distance from the sealing surface of one of the jaw members, e.g., jaw member 120, to yield a consistent and accurate gap distance between jaw members 110 and 120. It is envisioned for the gap distance between jaw members 110 and 120 during sealing should be in the range from about 0.001 inches to about 0.006 inches and, more preferably, between about 0.002 and about 0.003 inches. Details relating to the gap distance and the stop members are disclosed in the above-identified commonly-owned incorporated applications.

Figure 2:
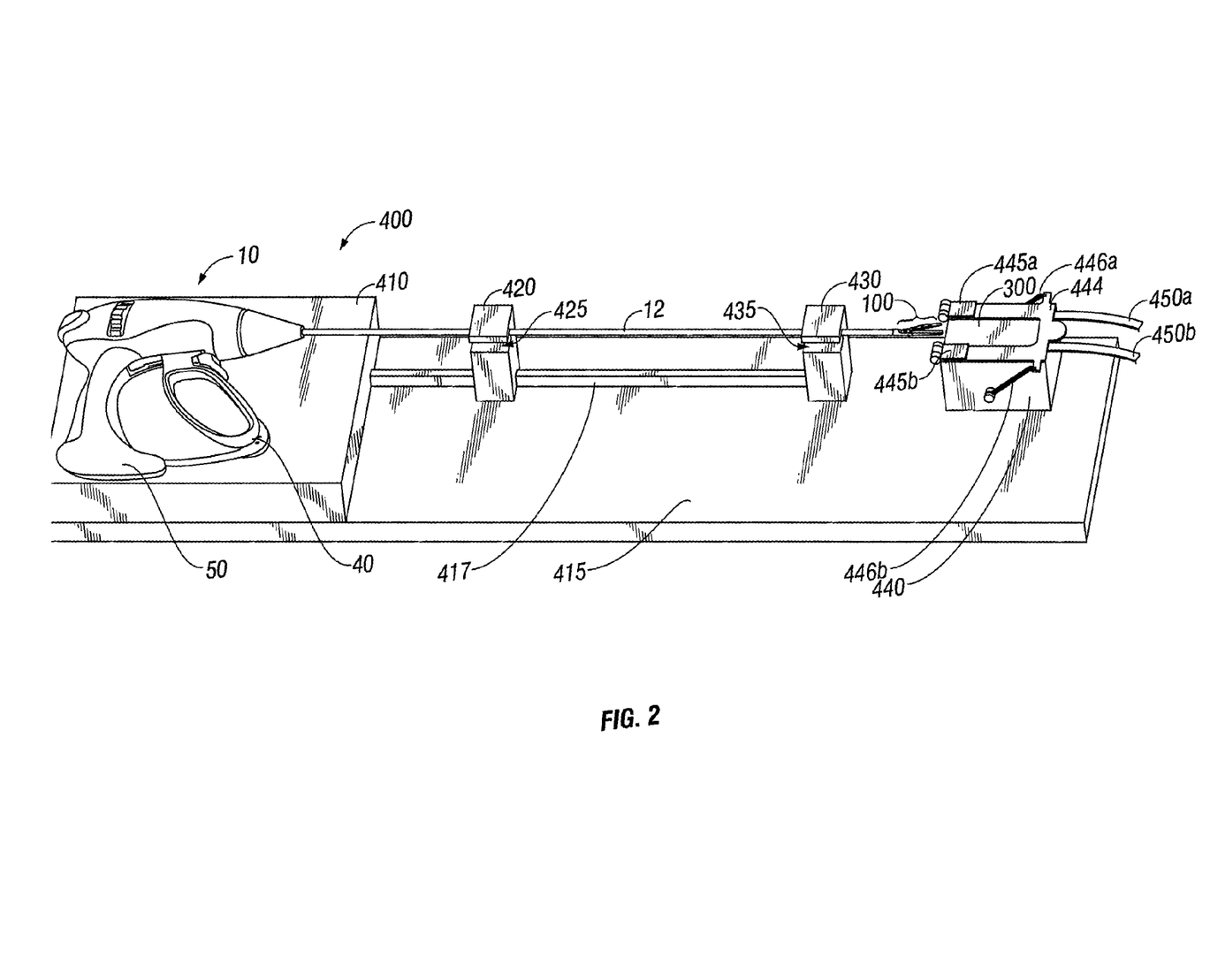
FIG. 2 is a side perspective view showing the forceps of FIG. 1 engaged within a testing fixture and prior to engagement with a testing material.

FIG. 2 shows the forceps 10 engaged atop a testing fixture or testing platform 400 according to the present disclosure which is configured to measure the closure pressure between jaw members 110 and 120 as part of a quality control test. For example, when a forceps 10 is assembled the forceps 10 is typically tested to assure that the mechanical cooperation of the drive assembly (not shown) and handle 40 yield a consistent closure force within the above-identified closure range. Obviously, only forceps 10 which pass the quality control are packaged for distribution.

The testing platform 400 includes an elongated bed 415, which is configured to support an instrument rest 410, a pair of selectively adjustable instrument supports 420 and 430 and a testing stand 440. More particularly, the instrument rest 410 is configured to support a variety of different endoscopic surgical forceps 10 of varying sizes and shaft lengths. The adjustable instrument supports 420 and 430 support the shaft 12 within a pre-defined notch or cavity 425 and 435, respectively, defined therein. The instruments supports 420 and 430 may include one or more quick release elements (not shown) which both adequately support and secure the shaft 12 during the testing period and also allow the user to quickly and easily engage a new forceps 10 for testing purposes. The supports 420 and 430 (or at least one support) are adjustable along a rail 417 to allow the testing technician to secure the shafts 12 of differently sized forceps 10 for testing purposes.

The testing platform 400 also includes a testing stand 440 which is generally positioned at a point distal to instrument stand 430. The testing stand 440 includes a generally U-shaped testing clamp 444, that is hingedly connected to the testing stand 440 by a pair of hinges 445a and 445b, to secure a testing material 300 atop testing stand 440. More particularly, the testing clamp 444 is selectively moveable from a first position (not shown) which enables a technician to load the testing material 300 atop the testing stand 440 to a second position which secures the testing material 300 atop the testing stand 440. A pair of springs 446a and 446b are included to bias the clamp 444 atop the testing stand 440 in a second position, i.e., a closed configuration, thus securing the testing material 300 in place for measuring purposes.

Figure 3:
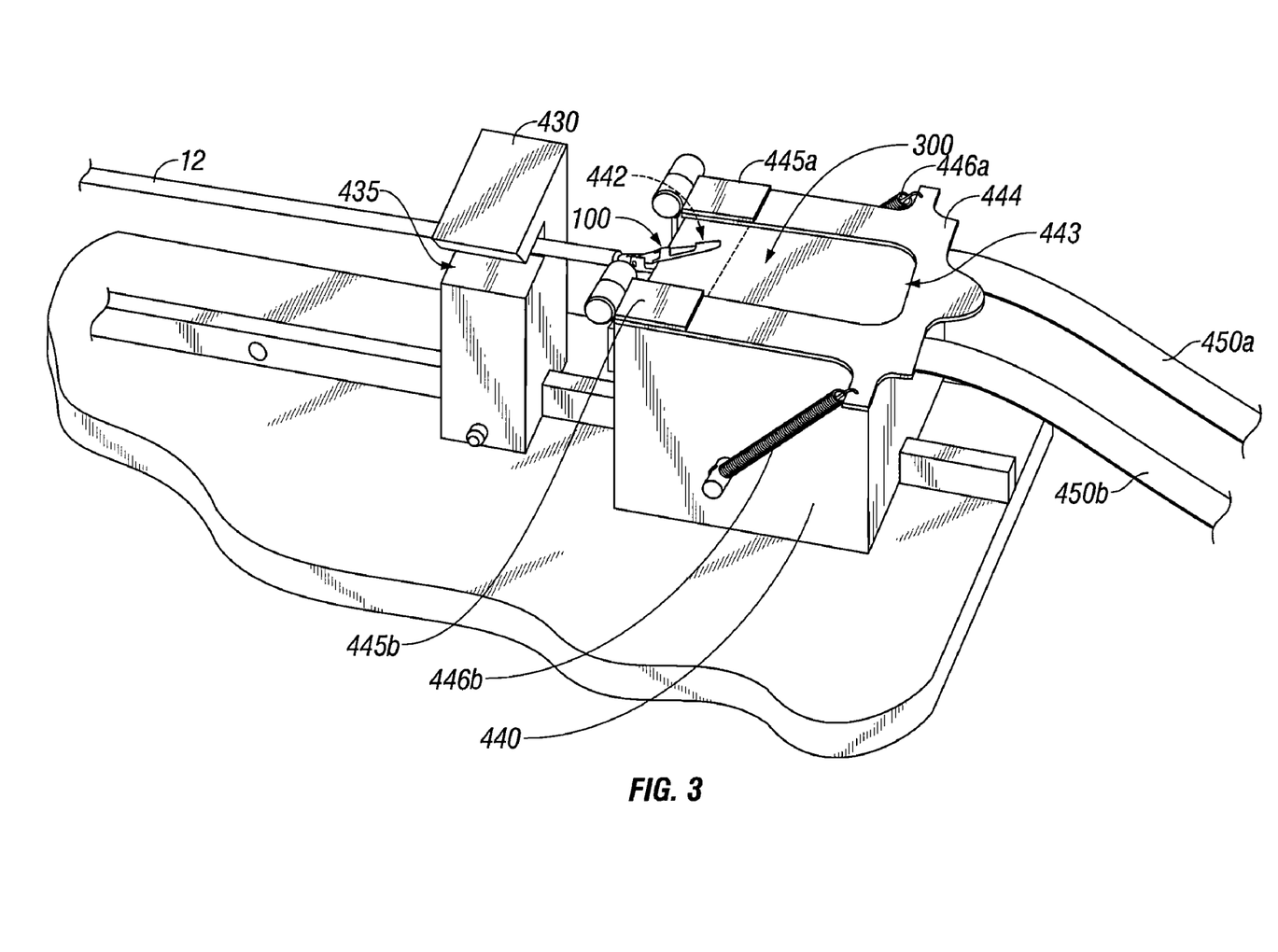
FIG. 3 is an enlarged perspective view of the forceps of FIG. 1 engaged within the test fixture showing the end effector assembly engaged about the testing material.
Figure 4:
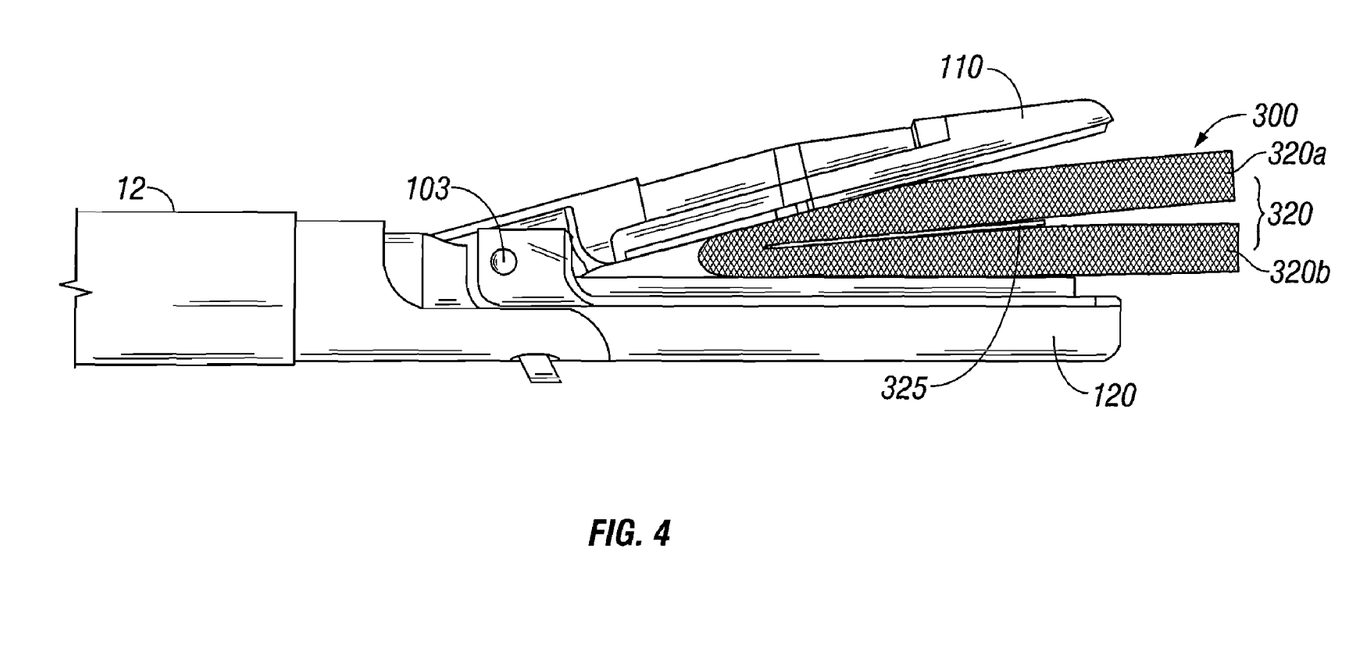
FIG. 4 is a greatly-enlarged side view of the end effector assembly of FIG. 1 shown engaged about the testing material.

As shown best in FIGS. 3 and 4, the testing material 300 includes a visco-elastic (or similar) material 320 which is designed to mimic certain properties of animal tissue, e.g., elasticity properties, tissue response properties under pressurized condition, thickness, moisture content, etc. In embodiments, the visco-elastic material is durable and is resistant to "wear and tear", e.g., visco-elastic fatigue, distortion, etc., over many testing cycles. The visco-elastic material is typically shaped or formed to include two opposing material layers 320a and 320b much like a vessel or artery. As a result, two layers of visco-elastic materials may be utilized to mimic tissue or one layer may be folded upon itself to mimic tissue (much like a vessel).

The testing material 300 also includes a pressure sensitive film 325 disposed between opposing material layers 320a and 320b which is disposed in operative communication with one or more electrical leads 450a and 450b (See FIG. 3). One envisioned pressure sensitive film suitable for this purpose is commonly sold by TekScan™ of South Boston, Mass. Leads 450a and 450b, in turn, connect to a meter, pressure gauge, computer diagnostic system or other display apparatus (not shown) to provide visual feedback to the technician relating to the closure pressure between the jaw members 110 and 120 when clamped.

For example, the TekScan™ system utilizes micro-electronics and an array of sensors along with Windows™-based software designed to allow the technician to receive immediate and/or real time visual feedback and analysis relating to the various pressure contours and dynamic and/or static pressure distributions across and along the surface area of the testing material 300 clamped between jaw members 110 and 120. TekScan™ is rated to accurately and repeatedly measure pressures up to about 200 psi without compromising reliability. It is contemplated that other ranges of pressure may be measured by other types of pressure sensitive films.

In use, the technician selects a forceps 10 for testing purposes or quality control purposes and places the forceps 10 atop the testing platform 400. The shaft 12 of the forceps 10 is engaged in the instrument supports 420 and 430 and moved into position to engage the testing material 300. The testing material 300 is loaded atop the testing stand 440 by opening the testing clamp 444 and placing the testing material 300 between clamp 444 and the testing stand 440. The clamp 444 is closed and locked to secure the testing material 300 atop the testing stand 440 such that a portion of the testing material 300 is accessible through a proximal window 443 defined in the testing clamp 444. The leads 450a and 450b from the pressure sensitive strip 325 are positioned to extend from the distal end of the testing stand 440 and connect to a meter or other diagnostic system (not shown).

To test the pressure distribution across and/or along the seal surfaces between opposing jaw members 110 and 120, the technician activates the testing meter or diagnostic system. The technician then moves handle 40 to open the jaw members 110 and 120 and moves the jaw members 110 and 120 on either side of the testing material 300 such that the testing material is positioned between the jaw members 110 and 120. The testing stand 440 includes a cavity 442 defined therein that is configured to facilitate engagement of the bottom jaw member 120 about the testing material 300. The jaw members 110 and 120 are then closed and clamped about the testing material 300 such that the handle 40 locks into engagement. Details relating to one envisioned releasable locking system for handle 40 is disclosed in the above-identified incorporated applications.

Once the testing material 300 is clamped, the pressure sensitive film operatively (e.g., electro-mechanically) communicates with the meter or other diagnostic display to provide an overall pressure reading, a pressure distribution and/or pressure contours (or maps) across and along the opposing surfaces of the jaw members 110 and 120. As can be appreciated this enables the technician to quickly and accurately determine whether the closure pressure of the forceps 10 falls within an acceptable pressure range. Moreover, the testing material 300 also enables the technician or instrument designer to assess changes in pressure distribution or pressure characteristics (high/low pressure points) of the opposing surfaces of the forceps 10 when certain design parameters are changed, adjusted, removed or otherwise modified, e.g., pivot point, closure angle, stop member configuration, degree of jaw taper, jaw deflection, knife channel design, variations in sealing surface roughness or flatness, or other design parameters commonly associated with vessel or tissue sealing. As a result, testing various new forceps 10 designs is greatly simplified.

When the testing platform 400 and testing material 300 are utilized for diagnostic and quality control purposes, the testing material 300 is typically designed to mimic or otherwise represent the various characteristics of human or animal tissue. On the other hand, if the testing material 300 and testing platform 400 are being used for instrument design purposes, it is contemplated that the testing material 300 may include multiple layers of visco-elastic material(s) of varying thickness, dimension and visco-elasticity to allow instrument designers to mimic all types of tissue. In some instances, more than one pressure sensitive film 325 may be utilized to test different areas of the surfaces of one or both jaw members 110 and 120, e.g., to provide various sensor points to test pressure across, along or anywhere proximate the jaw surfaces under varying conditions.

The present disclosure also relates to a method for testing the closure pressure of a forceps and includes the initial step of providing a forceps 10 for testing purposes having an end effector assembly 100 including two opposing jaw members 110 and 120 and providing testing fixture 400 having an elongated bed 415 which supports an instrument rest 410, a pair of selectively adjustable instrument supports 420 and 430 and a testing stand 440. The method also includes the step of providing a testing material 300 including two or more layers of visco-elastic material 320 having a pressure sensitive film 325 disposed between layers. The pressure sensitive film 325 is adapted to connect to a visual display (not shown).

The method also includes the steps of: engaging and securing the testing material 300 upon the testing stand 440; opening the jaw members 110 and 120 of the end effector assembly 100 to engage the testing material 300; closing and clamping the jaw members 110 and 120 about the testing material 300; and analyzing the pressure distribution between the opposing jaw members 110 and 120. The method may also include the step of verifying that the pressure between the jaw members 110 and 120 is between about 3 kg/cm$^2$ to about 16 kg/cm$^2$ or, desirably, between about 7 kg/cm$^2$ to about 13 kg/cm$^2$.

The present disclosure also relates to a testing system for measuring the closure pressure between opposing jaw members of an electrosurgical forceps. The testing system includes a testing platform including an elongated bed which supports an instrument rest thereon. The instrument rest, in turn, supports the electrosurgical forceps. A pair of selectively adjustable instrument supports are operatively associated with the elongated bed and positioned to secure the forceps atop the elongated bed. A testing stand is included which is disposed at a distal end of the elongated bed and configured to support at least one piece of testing material thereon. The testing material includes at least one layer of visco-elastic material configured to form a pocket therebetween and a pressure sensitive film disposed within the pocket of the visco-elastic layer. The pressure sensitive film is adapted to electro-mechanically communicate with a diagnostic system (not shown) to measure the closure pressure between jaw members when the jaw members are disposed in a clamped configuration.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A testing system for measuring a closure pressure between opposing jaw members of an electrosurgical forceps, the testing system comprising:
   a testing platform including an elongated bed that supports an instrument rest thereon, the instrument rest configured to support the electrosurgical forceps;
   a pair of selectively adjustable instrument supports operatively associated with the elongated bed and positioned to secure the forceps atop the elongated bed; and
   a testing stand disposed at a distal end of the elongated bed and configured to support at least one piece of testing material thereon, the testing material including:
      at least one layer of visco-elastic material configured to form a pocket therebetween; and
      a pressure sensitive film disposed within the pocket of the visco-elastic layer, the pressure sensitive film adapted to electro-mechanically communicate with a diagnostic system to measure the closure pressure between jaw members when the jaw members are disposed in a clamped configuration.

2. The testing system according to claim 1, wherein the instrument supports each define a notch configured to support a shaft of the electrosurgical forceps therewithin.

3. The testing system according to claim 1, wherein the testing stand includes a testing clamp configured to secure the testing material to the testing stand.

4. The testing system according to claim 3, wherein the testing clamp is hingedly connected to the testing stand by at least one hinge.

5. The testing system according to claim 3, wherein the testing clamp is selectively moveable between an open position and a closed position, wherein when the testing clamp is in the open position the testing material is insertable therein, and when the testing clamp is in the closed position the testing material is secured therein.

6. The testing system according to claim 5, wherein the testing clamp is biased to the closed position.

7. The testing system according to claim 6, wherein the testing clamp is U-shaped to define an area such that when the testing material is secured to the testing clamp, at least a portion of the testing material is exposed in the area of the testing clamp.

8. The testing system according to claim 1, wherein the visco-elastic material is configured to include two opposing material layers.

9. The testing system according to claim 8, wherein the pressure sensitive film disposed between the two opposing material layers is in operative communication with at least one electrical lead.

10. The testing system according to claim 9, wherein the at least one lead is configured to connect to a group consisting of a meter, a pressure gauge, and a computer diagnostic system and a display apparatus.

11. A testing system for measuring a closure pressure between opposing jaw members of an electrosurgical forceps, the testing system comprising:
   a testing platform including an elongated bed, the platform being configured to support the electrosurgical forceps;
   a pair of selectively adjustable instrument supports operatively associated with the elongated bed and positioned to secure the forceps relative to the platform; and
   a testing stand disposed at a distal end of the elongated bed and configured to support a testing material thereon, the testing material including a visco-elastic material supporting a pressure sensitive film, the pressure sensitive film adapted to electro-mechanically communicate with a diagnostic system to measure the closure pressure between the jaw members when the jaw members are disposed in a clamped configuration on the testing material.

12. The testing system according to claim 11, wherein the testing stand includes a testing clamp configured to secure the testing material to the testing stand.

13. The testing system according to claim 12, wherein the testing clamp is hingedly connected to the testing stand by at least one hinge.

14. The testing system according to claim 12, wherein the testing clamp is selectively moveable between an open position and a closed position, wherein when the testing clamp is in the open position the testing material is insertable therein, and when the testing clamp is in the closed position the testing material is secured therein.

15. The testing system according to claim 14, wherein the testing clamp is biased to the closed position.

16. The testing system according to claim 15, wherein the testing clamp is U-shaped to define an area such that when the testing material is secured to the testing clamp, at least a portion of the testing material is exposed in the area of the testing clamp.

17. A method for testing a closure pressure of an electrosurgical forceps, comprising the steps of:
   providing a forceps having an end effector assembly including two opposing jaw members;
   providing a testing fixture configured to support the forceps;
   providing a testing material including at least two layers of visco-elastic material having a pressure sensitive film disposed between the layers;
   securing testing material to the testing stand;
   opening the jaw members of the end effector assembly to receive the testing material;
   closing and clamping the jaw members onto the testing material; and
   analyzing a pressure distribution between the opposing jaw members.

18. The method according to claim 17, further comprising the step of:
   verifying that the pressure between the jaw members is between about 3 kg/cm$^2$ to about 16 kg/cm$^2$.

19. The method according to claim 18, further comprising the step of:
   verifying that the pressure between the jaw members is between about 7 kg/cm$^2$ to about 13 kg/cm$^2$.

20. The method according to claim 17, further comprising the step of:
   connecting the pressure sensitive film to a visual display.

21. The method according to claim 17, further comprising the step of:
   supporting a shaft of the forceps in or on at least one support of the test fixture.

22. The method according to claim 17, further comprising the step of:
   providing a test fixture having a pair of supports configured to support the shaft of the forceps.

23. The method according to claim 17, further comprising the step of:
   adjusting a location of the supports along a length of the shaft.

* * * * *